| United States Patent [19] | [11] Patent Number: 4,666,829 |
|---|---|
| Glenner et al. | [45] Date of Patent: May 19, 1987 |

[54] POLYPEPTIDE MARKER FOR ALZHEIMER'S DISEASE AND ITS USE FOR DIAGNOSIS

[75] Inventors: George G. Glenner, La Jolla; Caine W. Wong, Cardiff, both of Calif.

[73] Assignee: University of California, Berkeley, Calif.

[21] Appl. No.: 734,660

[22] Filed: May 15, 1985

[51] Int. Cl.$^4$ .................. G01N 33/566; C12Q 1/68
[52] U.S. Cl. ........................................ 435/6; 435/7; 435/68; 435/172.2; 436/501; 436/503; 436/504; 436/63; 436/548; 935/78; 935/110; 530/324; 530/328; 530/344; 530/806; 536/27
[58] Field of Search ............... 530/324, 328, 344, 806, 530/808, 810; 935/95, 78, 103, 110, 78; 435/7, 6, 68, 172.2, 948; 424/88; 436/548, 63, 501, 504, 503; 536/27

[56] References Cited

PUBLICATIONS

Kohler, et al., Nature, vol. 256, (1975), pp. 495–497.
Weir, D. M., Handbook of Experimental Immunology, third edition, (1979), Blackwell Scientific Pub., p. 28.20.
Glenner, et al., Biochem. Biophys. Res. Comm., vol. 120, No. 3, (1984), pp. 885–890.
Linke, R. P., et al., "Isolation of a Low-Molecular-Weight Serum Component Antigenically Related to an Amyloid Fibril Protein of Unknown Origin," Proc. Nat. Acad. Sci. 72:1473–1476 (1975).
Sipe, J. D., et al., "Amyloid Fibril Protein AA: Purification and Properties of the Antigenically Related Serum Component as Determined by Solid Phase Radioimmunoassay," J. Immunol. 116:1151–1156 (1976).
Igbal, K. et al., "Chemical Relationship of the Paired Helical Filaments of Alzheimer's Dementia to Normal Human Neurofilaments and Neurotubules," Brain Res. 142:321–332 (1978).
Glenner, G. G., et al., "Congophilic Microangiopathy in the Pathogenesis of Alzheimer's Syndrome (Presenile Dementia)" Med. Hypoth. 5:1231–1236 (1979).
Glenner, G. G., "Amyloid Deposits and Amyloidosis" New England J. of Med. 302:1283–1292 and 1333–1343 (1980).
Fujihara, S., et al., "Identification and Classification of Amyloid in Formalin-Fixed, Paraffin-Embedded Tissue Sections by the Unlabeled Immunoperoxidase Method" Lab. Invest. 43:358–365 (1980).
Selkoe, D. J., "Altered Protein Composition of Isolated Human Cortical Neurons in Alzheimer's Disease" Annals of Neurol. 8:468–478 (1980).
Glenner, G. G. et al., "Congophilic Angiopathy in the Pathogenesis of Alzheimer's Degeneration" Annals of Pathol. 1:120–129 (1981).
Selkoe, D. J., et al., "Myelin Basic Protein in Alzheimer Disease Neuronal Fractions and Mammalian Neurofilament Preparations" Annals of Neurol. 10:429–436 (1981).
Glenner, G. G., "Amyloidosis: The Hereditary Disorders, Including Alzheimer's Disease" J. Lab. and Clin. Med. 98:807–810 (1981).
Glenner, G. G., "Alzheimer's Disease (Senile Dementia): A Research Update and Critique with Recommendations" J. Am. Geriatrics Soc. 30:59–62 (1982).
Selkoe, D. J., "Alzheimer's Disease: Insolubility of Partially Purified Paired Helical Filaments in Sodium Dodecyl Sulfate and Urea" Science 215:1243–1245 (1982).
Anderton, B. H., et al., "Monoclonal Antibodies Show that Neurofibrillary Tangles and Neurofilaments Share Antigenic Determinants" Nature 298:84–86 (1982).
Glenner, G. G., "Alzheimer's Disease: Multiple Cerebral Amyloidosis" Banbury Report 15: Biological Aspects of Alzheimer's Disease, 1983 Cold Spring Harbor Laboratory, pp. 137–144.
Glenner, G. G., "Alzheimer's Disease-The Commonest Form of Amyloidosis" Arch. Pathol. Lab. Med. 107:281–282 (1983).
Allsop, D., et al., "The Isolation and Amino Acid Composition of Senile Plaque Core Protein" Brain Research 259:348–352 (1983).
Glenner, G. G., et al., "Alzheimer's Disease: Initial Report of the Purification and Characterization of a Novel Cerebrovascular Amyloid Protein" Biochem. Biophys. Res. Comm. 120:885–890 (1984).
Glenner, G. G. et al., "Alzheimer's Disease and Down's Syndrome: Sharing of a Unique Cerebrovascular Amyloid Fibril Protein" Biochem. Biophys. Res. Comm. 122:1131–1135 (1984).
Kidd, J. et al., "Senile Plaque Amyloid, Paired Helical Filaments, and Cerebrovascular Amyloid in Alzheimer's Disease are all Deposits of the Same Protein" The Lancet 1:278 (1985).
Nikaido, T. et al., "Studies in Ageing of the Brain" Arch. Neurol. 25:198–211 (1971).

*Primary Examiner*—Christine M. Nucker
*Assistant Examiner*—Stephen C. Wieder
*Attorney, Agent, or Firm*—Irell & Manella

[57] ABSTRACT

A novel polypeptide, Alzheimer's Amyloid Polypeptide (AAP), is provided in substantially purified form which is isolated from amyloid deposits in patients with Alzheimer's Disease. The polypeptide has the following amino acid sequence:

$H_2N$—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH.

The polypeptide, or fragments thereof, may be used to produce antibodies useful in a diagnostic test for Alzheimer's Disease. Nucleotide probes corresponding to portions of the polypeptide are also useful for diagnostic purposes.

41 Claims, No Drawings

POLYPEPTIDE MARKER FOR ALZHEIMER'S DISEASE AND ITS USE FOR DIAGNOSIS

BACKGROUND OF THE INVENTION

This invention relates generally to the diagnosis of Alzheimer's Disease in humans and, more specifically, to a novel polypeptide and antibodies and nucleotide probes corresponding thereto for use in diagnostic tests.

Alzheimer's Disease is a degenerative brain disorder characterized clinically by loss of memory, confusion, gradual physical deterioration and ultimately death. The etiology of the disease is virtually unknown but has been variously attributed to viruses, toxins, concentrations of heavy metals, as well as genetic defects. It is now estimated to afflict some two million Americans, most of them elderly. The disease is at present incurable and, amongst diseases, constitutes the fourth leading cause of death in this country.

The brains of individuals with Alzheimer's Disease exhibit characteristic lesions termed neurofibrillary tangles and neuritic plaques. These result from deposits of amyloid protein within or between the neurons. Recently, it has developed that similar deposits also line the walls of the cerebral blood vessels.

Until quite recently, Alzheimer's Disease was thought to account for relatively few of the cases generally classified as senile dementia. Other factors which can lead to such a condition include repetitious small strokes, thyroid disorders, alcoholism and deficiencies of certain vitamins, many of which are potentially treatable. Until this time, there has been no useful diagnostic test for Alzheimer's Disease. A definitive diagnosis is possible only postmortem or during life through a brain biopsy to reveal the presence of the characteristic plaques, tangles and cerebrovascular deposits which characterize the disorder. Such an invasive surgical procedure is inherently dangerous and is therefore rarely utilized. As a result, the clinical misdiagnosis of Alzheimer's Disease is estimated to be approximately 20%–30%.

Therefore, there exists a need for a definitive diagnostic test which can be performed on individuals suspected of having or being at risk for Alzheimer's Disease. Desirably, such a method should be relatively simple, sensitive, accurate and painless for the patient. Additionally, it should be highly specific in distinguishing Alzheimer's Disease from other disorders. It should be non-invasive so as not to require the painful and often hazardous removal of brain tissue samples. Furthermore, it is desirable that it be capable of being reduced to a standardized format, preferably easily and quickly performed. Additionally, because of the immense numbers of individuals potentially afflicted with the disease, it is desirable that such a test be relatively inexpensive to administer. The present invention satisfies such needs and provides further advantages.

BRIEF SUMMARY OF THE INVENTION

According to a principal aspect of the present invention, there is provided a novel polypeptide which is advantageously used as a marker for Alzheimer's Disease. The polypeptide can be used to obtain antibodies which will recognize antigenic determinants of the polypeptide or homologous polypeptides in tissues or body fluids and which may be used in a specific immunologic diagnostic test for Alzheimer's Disease. Further, the polypeptide can be used to produce a nucleotide probe which can hybridize with the gene which codes for this or a homologous polypeptide. Such a probe can also be utilized in a specific diagnostic test for the disease.

In accordance with the present invention, there is provided a purified polypeptide which may be characterized as having a molecular weight of about 4,200 Daltons as determined from gel exclusion column chromatography, and by its major L-amino acid sequence in which there may be minor additions or substitutions depending upon the source. The polypeptide can be further characterized by its relative mobility on disc electrophoresis with a 15% polyacrylamide gel and its chromatographic peak profile on high performance liquid chromatography at 36% acetonitrile. The polypeptide is isolated from cerebrovascular amyloid deposits in patients with Alzheimer's Disease through techniques involving differential centrifugation, gel exclusion column chromatography and high performance liquid chromatography. The polypeptide is hereinafter referred to as the Alzheimer's Amyloid Polypeptide or AAP.

As an additional aspect of the invention, the AAP polypeptide is solubilized in a basic guanidine solution which denatures the amyloid fibrils. In its native form, AAP exists in a so-called β-pleated sheet polypeptide conformation, which is highly insoluble. As such, it is extremely difficult to manipulate biochemically. Solubilization, however, results in a number of significant consequences. In a purified and solubilized state, AAP can be used to raise antibodies, using either another species of animal, such as a rabbit, or a hybridoma cell line. The resulting antibodies are specific for AAP and can be used in diagnostic tests such as, for example, histochemical staining of tissue samples or an immunoassay.

Further, it has been found that antigenic potential resides in fragments of the whole AAP molecule. Such fragments are hereinafter termed Polypeptide Fragments, or PF. Thus, it is possible to raise antibodies that specifically recognize AAP using a fragment of the polypeptide, as for example the N-terminal decapeptide. The resulting antibodies can themselves be used in diagnostic tests.

Additionally with the determination of the amino acid sequence of AAP, it is possible to ascertain the base sequence of the gene coding for AAP. A nucleotide probe can be constructed which will recognize and hybridize with the gene so as to provide a further diagnostic test which may determine a genetic predisposition, even in individuals who are not presently synthesizing the polypeptide. Alternatively, a probe can be constructed which recognizes messenger RNA (mRNA) corresponding to the gene and polypeptide.

It will be appreciated from the foregoing that the present invention provides a novel polypeptide which is a marker for Alzheimer's Disease. With this polypeptide, antibodies can be obtained which render possible a blood or tissue immunologic assay for the disease. Moreover, by utilizing the polypeptide to develop a nucleotide probe, it is possible to construct a diagnostic test which is effective even in the absence of expression of the polypeptide.

Other features and advantages of the present invention will become apparent from the following more detailed description which illustrates, by way of example, the principles of the invention.

DETAILED DESCRIPTION OF THE PREFERRED EMBODIMENT

As indicated above, the invention involves a novel purified polypeptide, its method of isolation and uses, and antibodies and nucleotide probes corresponding thereto, or to a fragment thereof. The polypeptide has been isolated from the cerebrovascular amyloid deposits of patients having Alzheimer's Disease, and represents a marker for the disorder. It can be characterized not only by its mobility in disc gel electrophoresis and high pressure liquid chromatography, but more conclusively, by its amino acid sequence.

The polypeptide isolated from the crerebrovascular amyloid deposits of patients with Alzheimer's Disease has been determined to have the following amino acid sequence:

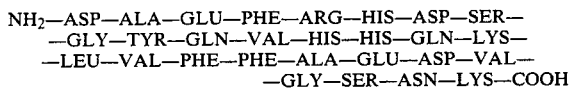

$NH_2$—ASP—ALA—GLU—PHE—ARG—HIS—ASP—SER—
—GLY—TYR—GLN—VAL—HIS—HIS—GLN—LYS—
—LEU—VAL—PHE—PHE—ALA—GLU—ASP—VAL—
—GLY—SER—ASN—LYS—COOH

In the above structures, the amino acid components of the peptides are identified by standardized abbreviations for convenience. These abbreviations are as follows:

| Amino Acid | Abbreviated Designation |
|---|---|
| L-arginine | ARG |
| L-alanine | ALA |
| L-glutamine | GLN |
| L-aspartic acid | ASP |
| L-glutamic acid | GLU |
| L-histidine | HIS |
| L-lysine | LYS |
| Glycine | GLY |
| L-leucine | LEU |
| L-phenylalanine | PHE |
| L-asparagine | ASN |
| L-serine | SER |
| L-tyrosine | TYR |
| L-valine | VAL |

Additions or substitutions may exist in the amino acid sequence depending on the source of the polypeptide. The present invention is not limited to the precise amino acid sequence, but is deemed to cover any such sequence variations or additions where the resulting polypeptide has the same function.

Brains obtained from patients suspected of having Alzheimer's Disease were frozen at autopsy. The tissues were histologically sectioned and stained with Congo red dye. When viewed through a polarizing microscope, amyloid deposits in and between the neurons and lining the cerebrovascular vessels appear apple green in tissues from Alzheimer's victims due to the birefringence of the conformation of the $\beta$-pleated sheet amyloid fibers. Only those brains exhibiting extensive cerebrovascular amyloidosis were utilized for AAP isolation. After removal of gross contaminants from the amyloid-laden vessels of the meninges, the meningeal tissues were homogenized and centrifuged to yield a brownish layer rich in amyloid fibrils. This layer was digested with collagenase, solubilized in 6M guanidine-HCl, pH 8.0 and centrifuged. The supernatant containing the solubilized polypeptide was desalted by dialysis; gel exclusion column chromatography and high performance liquid chromatography were used to purify the polypeptide. The amino acids of the purified AAP were sequentially cleaved in an automated amino acid sequencer and analyzed by high performance liquid chromatography in order to determine the amino acid sequence of AAP.

Purified AAP can be used to raise either polyclonal or monoclonal antibodies. The solubilized polypeptide is injected into rabbits and the resulting antibodies recovered from the serum. Alternatively, monoclonal antibodies may be produced by immunization of mice with either AAP or PF and fusion of their splenic cells with mouse myeloma cells.

The N-terminal decapeptide sequence alone has been determined to have antigenic specificity. The sequence may be produced synthetically using available amino acid synthesizers. Antibodies raised by use of the N-terminal decapeptide will selectively bind to amyloid fibrils in the neuritic plaques and cerebrovascular amyloid deposits.

Antibodies to either the whole AAP molecules or to such fragments as the N-terminal decapeptide can be used in standardized immunoassays, such as radioimmunoassays (RIA) and enzyme-linked immunosorbent assays (ELISA). For example, in a competitive test, known quantities of labelled AAP and antibodies to AAP or the N-terminal decapeptide are combined with a sample of serum from a patient, and the antigen-antibody complexes separated. The percent of labelled complexes can be used to determine the amount of AAP in the patient's serum.

Having established the amino acid sequence of AAP, a nucleotide probe can be constructed which is complementary to the DNA or mRNA coding for AAP or a portion thereof. Such a probe can then be used as an additional diagnostic test for the disease, or for a predisposition to the disease in individuals who may not express the polypeptide.

EXAMPLE I

Amyloid Fibril Concentration

Human brains of Alzheimer's Disease victims obtained at autopsy were frozen at $-70°$ C. Histological sections were taken, stained for amyloid using Congo red dye (Kodak) and only those with extensive cerebrovascular amyloidosis as indicated by birefringence under polarized light were selected for amyloid fibril isolation. Age-matched normal brains were used for controls. Gross cortical contaminants were removed from the meninges and the meningeal tissue, which contains amyloid-laden vessels, was homogenized in 0.09% sodum chloride-0.1% sodium azide. The homogenate was centrifuged in a Sorvall RC-5B (DuPont Instruments) at $12,500 \times g$ for 60 minutes at $4°$ C. and the supernatant discarded. The resultant pellet was made up of two visually distinct layers; the thin brownish top layer was enriched in amyloid fibrils as monitored by polarization microscopy after Congo red staining. The frozen pellet was dissected to separate the two layers. A second homogenization and centrifugation of the lower layer yielded additional amyloid fibrils. The combined amyloid-rich material was homogenized in 0.05M Tris-HCl, 3 mM $NaN_3$, 0.01 mM $CaCl_2$, pH 7.5 buffer to make an approximate 4% solution (weight/volume). Solid collagenase (EC 3.4.24.3 Sigma Chemical type 1) was added in a 1:100 ratio (weight enzyme: weight pellet) and the resultant mixture incubated in a Dubnoff shaker bath at $37°$ C. for 8 hrs. The extent of digestion by collagenase was monitored by Congo red staining with polarization microscopy. After the digestion was completed, the mixture was centrifuged in a Beckman L5-50B Ultracentrifuge at 105,000×g for 60 min. at 4° C. The supernatant was discarded and the pellet frozen at −20° C.

EXAMPLE II

Polypeptide Extraction

The collagenase-treated pellet was solubilized by adding about 80 mg of pellet to 20 ml of 6M guanidine-HCl, 0.1M Tris-HCl, 24 mM dithiothreitol, 0.34 mM EDTA, pH 8.0, and stirring at room temperature for 48 hours. After 48 hours the solution was centrifuged in a Beckman L5-50B Ultracentrifuge at 105,000×g for 60 min. at 4° C. The pellet was separated from the supernatant. The supernatant was placed into 1000 molecular weight cut-off dialysis tubing (Spectra/Por 6, Fisher Scientific) and dialyzed for such time necessary to reduce the ionic strength of the solution to about 0. The solution remaining in the dialysis tubing was then lyophilized and the resulting powder dessicated and stored at −70° C.

EXAMPLE III

SDS-urea Polyacrylamide Gel Electrophoresis (SDS-urea Page)

In order to further define the polypeptide, SDS-urea polyacrylamide gel electrophoresis (PAGE) was performed according to the method of Laemmli (Nature, 227:680 1970), modified only by the addition of 8M urea in the stacking and resolving gel. Slab gels (15%) were made 0.75 mm thick and run at 10 mA constant current. After electrophoresis, gels were stained with Coomassie Brilliant Blue R. These gels exhibited a band corresponding to a polypeptide of approximately 4,800 Daltons which compares favorably with the molecular weight obtained for the polypeptide from gel exclusion column chromatography. This polypeptide appeared only in those lanes of the electrophoretic gel in which amyloid-laden material from patients with Alzheimer's Disease was applied. Lanes in which control material was applied lacked a corresponding band.

EXAMPLE IV

G-100 Sephadex Gel Exclusion Column Chromatography

Forty mg of the extracted material from Example II were dissolved in 3 ml of 6M guanidine-HCl 0.1M Tris-HCl, pH 8.0, and 24 mM dithiothreital and applied to a 2.5×100 cm calibrated G-100 Sephadex column (Pharmacia) equilibrated with 5M guanidine-HCl, 1N acetic acid. The column was calibrated with cytochrome C (horse heart), 12,384 $M_r$ and glucagon, 3,485 $M_r$. The polypeptide elution profile was monitored at 280 nm with a Beckman 35 Spectrophotometer. The polypeptide peak centered at 4,200 $M_r$ was pooled and dialyzed exhaustively against deionized water to reduce the ionic strength to about 0, lyophilized and stored dessicated at −70° C.

EXAMPLE V

High Performance Liquid Chromatography (HPLC)

One hundred μg of the lyophilized polypeptide from peak fractions of the Sephadex column were solubilized into 25 μl of 5M guanidine-HCl, 1N acetic acid. This was injected into a HPLC (Waters) system. The mobile phase was: solvent A: 0.1% trifluoroacetic acid/H₂O, solvent B: 100% acetonitrile. The gradient was linear from 10% to 50% solvent B over 60 min. Flow rate was 0.8 ml/min. and the polypeptide peaks were detected at 229 nm with 2.0 AUFS (Absorbance Units Full Scale). The stationary phase was a Vydac 214TP54 C₄ peptide column. Three major polypeptide peaks were found that had no correspondence with control samples, one at 36% solvent B and the others at about 35% solvent B. These polypeptide peaks were pooled separately, lyophilized and stored at −70° C.

EXAMPLE VI

Amino Acid Sequencing

HPLC purified samples were dissolved in heptofluorobutyric acid and loaded in a Beckman 890 C spinning cup sequencer. The collected antilothiazolone amino acids were converted to phenylthiohydantoin amino acids (PTH-amino acids) with 1N HCl/MeOH at 50° C. for 10 min. The PTH-amino acids were dried and redissolved in MeOH, and analyzed on a Beckman 322 HPLC system fitted with a ETH-Permaphase guard column and an IBM 6μ CN column in line. The eluent was monitored at 254 nm. The resulting amino acid sequence of the polypeptide was thus determined to be:

NH₂—ASP—ALA—GLU—PHE—ARG—HIS—ASP—SER—
—GLY—TYR—GLN—VAL—HIS—HIS—GLN—LYS—
—LEU—VAL—PHE—PHE—ALA—GLU—ASP—VAL—
—GLY—SER—ASN—LYS—COOH

EXAMPLE VII

Synthesis of the Peptide Fragment

A synthetic peptide (PF) with the sequence consisting of the first 10 residues of the AAP protein (ASP-ALA-GLU-PHE-ARG-HIS-ASP-SER-GLY-TYR) was synthesized according to the method of Marglin and Merrifield (Ann. Rev. Biochem. 39:841 1970), which is incorporated by reference, using a Beckman Systems 990 Peptide Synthesizer. A cysteine residue was added to the carboxyl terminus for coupling the peptide to a carrier protein.

EXAMPLE VIII

Coupling to Keyhole Limpet Hemocyanin

PF was coupled to the immunogenic carrier, keyhole limpet hemocyanin (KLH), through the terminal cysteine residue. Sixteen mg of KLH were dissolved in 1.0 ml 10 mM NaH₂PO₄, pH 7.2 and 2.4 mg of m-maleimidobenzoyl-N-hydroxysuccinimide ester (MBS) dissolved in 25 μl dimethylformamide was added dropwise to the KLH solution while stirring continuously at room temperature for 30 min. The resulting solution was dialyzed against 3×1 liter 50 mM NaH₂PO₄, pH 6.0 over 12 hrs. at 4° C. After dialysis, the contents of the dialysis tubing was centrifuged at 13K×g for 10 min. to remove undissolved particulates. The protein concentration of the MBS activated KLH solution was determined by the Lowry Method (J. Biol. Chem. 193:263 1951). Five mg of the peptide fragment was dissolved in 0.5 ml Tris buffered saline, pH 8.0. To this solution, 3.2 mg of the MBS activated KLH solution were added dropwise while stirring. The pH was adjusted to 7.2 and the stirring continued at room temperature for 3 hrs. The coupling efficiency was determined to be between 41%-80% for different preparations.

EXAMPLE IX

Immunization

Antibodies can be raised to either AAP or PF in mammals such as rabbits, goats and mice. In the preferred embodiment, five 10-week old female BALB/c mice were injected intraperitoneally with 4 µg PF coupled to KLH (PF-KLH) in Freund's complete adjuvant (Sigma). The mice was boosted 14 days later with 4 µg PF-KLH in Freund's incomplete adjuvant (Sigma). Three weeks after initial immunization, the mice were boosted once more with 1.0 µg PF-KLH IN 10 mM Tris, 150 mM NaCl, pH 8.0. Serum was obtained 7 days after the final boost.

The specificity of antiserum for AAP and PF was tested. A limiting dilution of the antiserum (1:6000) was preincubated with varying concentrations of PF and an unrelated 17 amino acid peptide at 4° C. for 12 hours and then used in a solid phase ELISA.

Antigens were dissolved in 35% acetonitrile −0.1% TFA/H$_2$O to a final concentration of 0.1 µg/25 µl. Aliquots of 25 µl of antigen were distributed to each well of 96 well polyvinyl chloride microtiter plates and left at room temperature to dry. These were stored dessicated at 4° C. until needed. Nonspecific binding sites were blocked with 2% ovalbumin in Tris buffered saline containing 0.2% Tween-20 and 0.01% Thimerosal, pH 8.0 (TBTT). Fifty µl of appropriate dilutions of primary antibodies were added to blocked test wells and incubated at room temperature for 30 minutes. Unbound antibodies were removed by washing the wells with freshly deionized H$_2$O followed by TBTT. Bounded primary antibody was detected by a second antibody, horseradish peroxidase conjugated goat anti-mouse antibodies (Capell). The second antibody was diluted according to manufacturer's recommendation and 50 µl aliquots added to test wells. These were incubated at room temperature for 30 minutes and washed as before. O-Phenylenediamine in 80 mM citrate-phosphate buffer, pH 6.5 was used as substrate for the conjugated peroxidase. Visible reaction products were quantified with an automated microtiter plate reader set at 492 nm.

Sera from all five immunized mice were found immunoreactive to AAP, PF and KLH and unreactive to control antigens. Normal mouse serum was unreactive to all antigens tested. The mouse serum with the highest titer ($A_{492}=1.94$ at 1:2000) against AAP was designated anti-AAP and used for all further work.

EXAMPLE X

Production of Monoclonal Antibodies

Hybridomas producing antibodies against PF were generated by standard murine fusion procedures as detailed in Kohler and Milstein (Nature 256:495 1975), which is incorporated by reference. Briefly, two immunized BALB/c mice were sacrificed and the spleens removed. Mixed splenocytes were obtained by pressing the spleens through a 30 mesh stainless steel screen. These were fused with P3X63Ag8 murine myeloma cells (aminopterin sensitive) at a fusion ratio of 10:1 in 35% polyethylene-glycol. These cells were plated out in 96 well tissue culture plates in the presence of 2×10$^6$ thymocytes/ml. Hybridomas were selected for by growing the cells in the presence of aminopterin poisoned Dulbecco's modified Eagle's media augmented with hypoxanthine, thymine and 10% fetal bovine serum. Hybidomas were screened for reactivity against PF and AAP protein via ELISA as described in Example XII. Positive clones called CW 1/1, CW 1/2 and CW 1/3 were expanded and subcloned twice. Aliquots of the clones were frozen and stored in liquid nitrogen. Supernatants from positive clones were produced in large quantities for further purification of monoclonal antibodies. A similar method is used to produce monoclonal antibodies to PF, where the mice are originally immunized with PF.

EXAMPLE XI

Immunohistochemistry

Localization of amyloid deposits was demonstrated with mouse anti-PF serum by the peroxidase anti-peroxidase method of Sternberger, L.A., 1979 Immunocytochemistry. Formalin fixed sections of autopsied brain tissues were obtained from patients with Alzheimer's Disease. Age-matched controls were also selected. Tissue sections 6.0 microns thick were fixed to glass slides. The sections were then challenged with the following series of antibodies with wash steps in between each: (1) Anti-PF as obtained in Example IX, or normal mouse serum at 1:2500 dilution in 1.0% ovalbumin-phosphate buffered saline, pH 7.5, (2) rabbit anti-mouse IgG at 1:1000, (3) swine anti-rabbit IgG at 1:1000, (4) rabbit peroxidase-anti-peroxidase at 1:1000 (Dakopatts). Positive immunoreaction was detected with 3,3'-diaminobenzidine (Sigma). Congo red dye (Kodak) staining followed and Mayer's hematoxylin (MCB Chemicals) was used as counterstain. For inhibition experiments, a 1:500 dilution of anti-AAP was preincubated with 1.0% PF or KLH in 20 mM Tris, 150 mM NaCl, 0.2% Tween-20, 0.01% Thimerosal, pH 8.0 for 12 hours at 4° C. prior to use in the procedure just outlined. A Leitz Orthoplan polarizing microscope was employed for visualization and photomicroscopy. Antibody to AAP or PF was found to localize to amyloid deposits in cerebral vessels and to neuritic plaques in patients with Alzheimer's Disease. No reaction was found in similarly treated tissues from normal controls. Preincubation of anti-AAP with KLH does not alter specific staining to amyloid in cerebral vessels and neuritic plaques, whereas preincubation with PF inhibits staining completely, indicating the anti-KLH antibodies did not contribute to the specific staining.

EXAMPLE XII

Use of the Antibody in a Diagnostic Immunoassay

The antibody corresonding to AAP or PF can be utilized in a diagnostic immunoassay using standard methods (see, for example, Campbell, D. H., et al., 1964 Methods in Immunology), such as a radioimmunoassay (RIA) of the competitive type. Flexible polyvinyl chloride microtitration plates with "U" bottom wells and 270 µl capacity (Cooke Engineering Co.) were coated with anti-AAP or anti-PF antibodies according to the method of Catt and Tregear (Science 158:1570 1969). AAP or PF were synthesized using a Beckman System 990, and labelled. A variety of labels can be employed, such as radiosiotopes, including $^{125}$I, $^3$H and $^{14}$C, enzymes, fluorescers or chemiluminescent molecules. In the preferred embodiment, $^{125}$I is incorporated into the polypeptide of fragment using Bolton-Hunter reagent (Sigma) (see Bolton and Hunter, Biochem. J. 133: 529 1973, which is incorporated by reference).

A known quantity of labelled AAP or PF is added to each well along with a known volume of body fluid, for example serum or cerebral spinal fluid, from a patient and allowed to incubate for a time sufficient to obtain binding between the AAP or PF (antigens) and the antibodies. The samples were then rinsed out and the wells cut out and placed in gamma counting vials. The bound radioactivity was determined with a gamma counter. The amount of bound radioactivity is inversely proportional to the amount of AAP or PF in the serum sample, since the labelled and unlabelled antigens compete for binding sites on the bound antibodies. Standardized samples can be run in control wells in order to obtain quantitative results.

EXAMPLE XIII

Oligonucleotide Probe Synthesis

Regions of the AAP amino acid sequence can be selected for construction of nucleotide probes. From the amino acid sequence, the mRNA sequence can be determined by knowledge of the genetic code. From the mRNA sequence, the coding of the DNA can be determined by knowledge of the base-pairing of nucleic acids. A probe made complementary to mRNA is useful in screening both "Southern" and "Northern" blots, procedures that will be described hereinafter. Because of the degeneracy of the genetic code, the exact nucleic acid seuence cannot be precisely deduced. To minimize the number of different possibilities, regions of the amino acid sequence are chosen that are rich in amino acids with single codons (methionine: AUG; tryptophan: UGG) or double codons (phenylalanine: UUU, UUC; tyrosine: UAU, UAC; histidine: CAU, CAC). A mixture of nucleotides that contain all possible coding combinations can be chemically synthesized simultaneously by standard methods. Only one of the coding combinations will be perfectly complementary.

For example, the sequences from amino acid 10 (TYR) to amino acid 16 (LYS) and from amino acid 20 (LYS) to amino acid 25 (GLY) result in the following nucleotide sequences:

Amino Acids 10 through 16:

```
5'-TTTTGATGATGAACTTGATA-3'
     C  G   G   G    C  . G
                     T
                     C
```

Amino acids 20 through 25:

```
5'-CCAACATCTTCAGCAAA-3'
      G  G  C  G   G
      T        T
      C        C
```

Each of the above sequences generates 128 different nucleotide sequences. One out of the 128 will be perfectly complementary to the DNA sequence coding for the AAP protein. Such a ratio is considered acceptable by those skilled in the art.

To select for the correct coding combination, the hybridization of the probe to the genome conditions can be adjusted to a point where only the perfectly complementary probe will be stably hybridized to the genomic DNA. Synthesis of nucleotides can be accomplished manually or by automated machines using the phosphodiester (Agarwal, et al., Angew. Chem. Int. Ed. 11:451 1972), phosphotriester (Hsiung, et al., Nucleic Acid Res. 6:1371 1979) or phosphoramidite (Beaucage and Caruthers, Tetrahedron Lett. 22:1859 1981) methods. The preferred method employs the latter technique and the model 380A DNA Synthesizer (Applied Biosystems). To identify the probe in use, the nucleotide can be labelled directly with atoms of $^{32}P$, $^{3}H$ or $^{14}C$ or fluorescers or indirectly with specific labelled antibodies. The preferred method attaches gamma $^{32}P$ dATP to the nucleotide by the action of $T_4$ polynucleotide kinase (Maxam and Gilbert, PNAS 74:560 1974).

EXAMPLE XIV

Use of the Probe for DNA Hybridization

In order to determine whether the gene for AAP exists in a given sample, the "Southern Blot" method can be used (Southern, J. Mol. Biol. 98:503 1975). A probe complementary to the DNA genomic sequence or a portion thereof is synthesized and labelled as in Example XIII. Total DNA from a tissue of a patient is isolated as described by Maniatis, et al. (Molecular Cloning: A Laboratory Manual, pp 545 1981). The DNA is cleved with a battery of selective restriction endonucleases that will leave intact the sequence complementary to the probe. The DNA fragments are separated by electrophoresis in an agarose gel. The DNA fragments are denatured by soaking the gel in 1.5 M NaCl and 0.5 NaOH. The denatured DNA fragments are transferred to a sterilized nitrocellulose filter by electrophoresis (Bittner, et al., Analytical Biochem. 102:459 1980) or by blotting as originally described by Southern, as cited above. The transfer techniques duplicates the restriction fragment pattern developed by electrophoresis in the gel onto the nitrocellulose filter.

The DNA spotted filter is washed, and dried at an elevated temperature so as to fix the DNA in position. Hybridization can be accomplished by any of several methods well known in the art (see, for example, Gall and Pardue, PNAS 63:378 1969, which is incorporated by reference). Essentially, the probe is applied to the filter in an inert polar organic solvent. Various factors can be varied in order to regulate the stringency of hybridization according to the degree of complementarity of the probe. These include, among others, temperature, probe concentration and time. The filter is then washed, dried and assayed from the particular label. Where the label employed is a radioisotope, the filter is exposed to x-ray film. Areas of exposure on the film indicate the presence of genomic DNA sequences complementary to the probe. Such a diagnostic test can indicate individuals possessing the gene, even in the absence of its expression.

Alternatively, the analogous "Northern Blot" method (Alwine, et al., Proc. Nat. Acad. Sci. USA 74:5350 1977) may be employed to determine whether mRNA sequences corresponding to AAP are present in a sample of a tissue in which the gene is expressed.

Although the invention has been described with references to the presently-preferred embodiment, it should be understood that various modifications can be made by those skilled in the art without departing from the invention. Accordingly, the invention is limited only by the following claims.

What is claimed is:

1. A substantially purified polypeptide isolated from patients with Alzheimer's Disease, Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH.

2. A composition comprising the substantially purified polypeptide of claim 1, solubilized in a basic guanidine solution.

3. A composition comprising the substantially purified polypeptide of claim 2, wherein the basic guanidine solution is 6M guanidine-HCl, having a pH of about 8.0.

4. A reagent for use in the diagnosis of Alzheimer's Disease in a human patient, comprising antibodies obtained by means of an immune response to exposure to the substantially purified polypeptide isolated from patients with Alzheimer's Disease, Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH.

5. The diagnostic reagent of claim 4, wherein the antibodies are polyclonal.

6. The diagnostic reagent of claim 4 wherein the immune response is produced in a mammal selected from the group consisting of rabbits, goats and mice.

7. The diagnostic reagent of claim 4 wherein the antibodies are monoclonal.

8. The diagnostic reagent of claim 4 wherein the immune response is produced in murine-murine hybridoma cells.

9. A diagnostic method for determining the presence of Alzheimer's Disease in a human patient by detecting the presence of Alzheimer's Amyloid Polypeptide in the patient through an immunoassay, comprising the steps of:
  a. combining a sample of the human patient's body fluid suspected of containing Alzheimer's Amyloid Polypeptide with antibodies specific to Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH;

b. monitoring the combination of step a. to determine whether said antibodies have bound to said Alzheimer's Amyloid Polypeptide in an immunological reaction, thereby indicating that said patient has Alzheimer's Disease.

10. The diagnostic method of claim 9, wherein said combining step further includes adding a known quantity of labelled Alzheimer's Amyloid Polypeptide, whereby a competitive immunoassay is established.

11. The diagnostic method of claim 10, wherein said label is capable of emitting radiation.

12. The diagnostic method of claim 11, wherein said label is ¹²⁵I.

13. A diagnostic method for determining the presence of Alzheimer's Disease in a human patient by histological localization of Alzheimer's Amyloid Polypeptide, comprising the steps of:
  a. combining a sample of the human patient's tissue with antibodies specific to Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH;

b. monitoring the combination of step a. to determine whether said antibodies have bound to said Alzheimer's Amyloid Polypeptide in an immunological reaction, thereby indicating that said patient has Alzheimer's Disease.

14. The diagnostic method of claim 13, wherein said combining step further includes adding a known quantity of labelled Alzheimer's Amyloid Polypeptide, whereby a competitive immunoassay is established.

15. The diagnostic method of claim 13, wherein said label is capable of emitting radiation.

16. The diagnostic method of claim 13, wherein said label is ¹²⁵I.

17. The diagnostic method of claim 14, wherein said label is a component of an enzymatic reaction.

18. A labelled nucleotide probe, comprising a sequence of nucleic acid substantially complementary to the nucleotide sequence coding for the substantially purified polypeptide isolated from patients with Alzheimer's Disease, Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH.

19. The nucleotide probe of claim 18, wherein the nucleotide sequence coding for said polypeptide is DNA.

20. A method of detecting individuals possessing a nucleotide sequence coding for the polypeptide of claim 1, comprising the steps of:
  a. providing a labelled nucleotide probe capable of selectively hybridizing with a portion of the nucleotide sequence coding for the substantially purified polypeptide isolated from patients with Alzheimer's Disease, Alzheimer's Amyloid Polypeptide, having the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

-continued

—VAL—GLY—SER—ASN—LYS—COOH;

b. exposing the nucleotide probe to a tissue sample from a patient;

c. monitoring the reaction of step b. for nucleic acid hybridization.

21. The method of claim 20, wherein said label is selected from the group consisting of $^{32}P$, $^{3}H$, and $^{14}C$.

22. An immunogenic peptide fragment of a substantially purified polypeptide isolated from patients with Alzheimer's Disease, Alzheimer's Amyloid Polypeptide, comprising:

a linear sequence of amino acids corresponding to any subsequence of the following amino acid sequence:

H₂N—ASP—ALA—GLU—PHE—ARG—HIS—ASP—

—SER—GLY—TYR—GLN—VAL—HIS—HIS—GLN—

—LYS—LEU—VAL—PHE—PHE—ALA—GLU—ASP—

—VAL—GLY—SER—ASN—LYS—COOH;

said linear sequence being immunogenic so as to induce the production of active antibodies specific to Alzheimer's Amyloid Polypeptide.

23. An immunogenic peptide fragment of substantially purified polypeptide isolated from patients with Alzheimer's Disease, Alzheimer's Amyloid Polypeptide, as recited in claim 22, wherein the peptide fragment is about 10 amino acids in length.

24. An immunogenic peptide fragment of a substantially purified polypeptide isolated from patients with Alzheimer's Disease, Alzheimer's Amyloid Polypeptide, as recited in claim 23, within the linear sequence of amino acids is as follows:

H₂N-ASP-ALA-GLU-PHE-ARG-HIS-ASP-SER-GLY-TYR-COOH.

25. A composition comprising the peptide fragment of a substantially purified polypeptide isolated from patients with Alzheimer's Disease, Alzheimer's Amyloid Polypeptide, as recited in claim 22, solubilized in a basic guanidine solution.

26. A composition comprising the peptide fragment of a substantially purified polypeptide isolated from patients with Alzheimer's Disease, Alzheimer's Amyloid Polypeptide, as recited in claim 22, coupled to an immunogenic carrier.

27. A reagent for use in the diagnosis of Alzheimer's Disease in a human patient, comprising antibodies obtained by means of an immune response to exposure to the peptide fragment as recited in claim 22.

28. The diagnostic reagent of claim 27, wherein the antibodies are polyclonal.

29. The diagnostic reagent of claim 27 wherein the immune response is produced in a mammal selected from the group consisting of rabbits, goats and mice.

30. The diagnostic reagent of claim 27, wherein the antibodies are monoclonal.

31. The diagnostic reagent of claim 27, wherein the immune response is produced in murine-murine hybridoma cells.

32. A diagnostic method for determining the presence of Alzheimer's Disease in a human patient, comprising the steps of:

a. combining a sample of body fluid from the patient with the antibodies obtained by means of an immune response to a peptide fragment as recited in claim 22 b. monitoring the combination of step a. to determine whether said antibodies have bound to said Alzheimer's Amyloid Polypeptide in an immunological reaction, thereby indicating that said patient has Alzheimer's Disease.

33. The diagnostic method of claim 32, wherein said combining step further includes adding a known quantity of the peptide fragment as recited in claim 32, which peptide fragment has been labelled.

34. The diagnostic method of claim 33, wherein said label is capable of emitting radiation.

35. The diagnostic method of claim 34, wherein said label is $^{125}I$.

36. The diagnostic method of claim 33, wherein said label is a component of an enzymatic reaction.

37. A diagnostic method for determining the presence of Alzheimer's Disease in a human patient by detecting the presence of Alzheimer's Amyloid Polypeptide in the patient through an immunoassay, comprising the steps of:

a. combining a sample of the patient's tissue suspected of containing Alzheimer's Amyloid Polypeptide with antibodies specific to a peptide fragment as recited in claim 22 b. monitoring the combination of step a. to determine whether said antibodies have bound to said Alzheimer's Amyloid Polypeptide in an immunological reaction, thereby indicating that said patient has Alzheimer's Disease.

38. The diagnostic method of claim 37, wherein said combining step further includes adding a known quantity of the immunogenic peptide fragment recited in claim 22, whereby a competitive immunoassay is established.

39. The diagnostic method of claim 38, wherein said label is capable of emitting radiation.

40. The diagnostic method of claim 39, wherein said label is $^{125}I$.

41. The diagnostic method of claim 38, wherein said label is a component of an enzymatic reaction.

* * * * *

UNITED STATES PATENT AND TRADEMARK OFFICE
CERTIFICATE OF CORRECTION

PATENT NO. : 4,666,829

DATED : May 19, 1987

INVENTOR(S) : George G. Glenner and Caine W. Wong

It is certified that error appears in the above-identified patent and that said Letters Patent is hereby corrected as shown below:

Column 3, line 14, delete "crerebrovascular" and insert therefor -- cerebrovascular --.

Column 7, line 11, delete "was" and insert therefor -- were --.

Column 9, line 30, delete "seuence" and insert therefor -- sequence --.

IN THE CLAIMS:

Claim 38.

Column 14, line 49, insert after "immunogenic" -- labelled --

Signed and Sealed this

Twenty-first Day of May, 1991

Attest:

HARRY F. MANBECK, JR.

*Attesting Officer*  *Commissioner of Patents and Trademarks*